(12) United States Patent  
Prins et al.

(10) Patent No.: US 7,863,022 B2
(45) Date of Patent: Jan. 4, 2011

(54) AMPLIFICATION OF NUCLEIC ACIDS WITH MAGNETIC DETECTION

(75) Inventors: Menno Willem Jose Prins, Eindhoven (NL); Aart Van Amerongen, Wageningen (NL); Maatje Koets, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 11/916,553

(22) PCT Filed: Jun. 7, 2006

(86) PCT No.: PCT/IB2006/051817

§ 371 (c)(1),
(2), (4) Date: Dec. 5, 2007

(87) PCT Pub. No.: WO2006/131892

PCT Pub. Date: Dec. 14, 2006

(65) Prior Publication Data

US 2008/0207464 A1 Aug. 28, 2008

(30) Foreign Application Priority Data

Jun. 9, 2005 (EP) .................................. 05105063
May 10, 2006 (EP) .................................. 06113752

(51) Int. Cl.
*C12Q 1/68* (2006.01)
*C12P 19/34* (2006.01)
(52) U.S. Cl. ........................... 435/91.2; 435/6; 435/91.1
(58) Field of Classification Search ........................ None
See application file for complete search history.

(56) References Cited

U.S. PATENT DOCUMENTS

| 5,888,779 | A | * | 3/1999 | Kacian et al. .............. 435/91.2 |
| 5,929,208 | A | * | 7/1999 | Heller et al. .................. 506/16 |
| 2002/0006643 | A1 | | 1/2002 | Kayyem et al. |
| 2002/0081714 | A1 | | 6/2002 | Jain et al. |
| 2002/0119470 | A1 | | 8/2002 | Nerenberg et al. |
| 2003/0143604 | A1 | | 7/2003 | Storhoff et al. |
| 2003/0215825 | A1 | | 11/2003 | Tong |

FOREIGN PATENT DOCUMENTS

| WO | 9610644 | 4/1996 |
| WO | 9907897 | 2/1999 |
| WO | 0061803 | 10/2000 |
| WO | 0114591 | 3/2001 |
| WO | 03054523 A2 | 7/2003 |
| WO | 2005007887 A1 | 1/2005 |
| WO | 2005010527 | 2/2005 |

(Continued)

OTHER PUBLICATIONS

Jeffrey Van Ness et al: "Isothermal Reactions for the Amplification of Oligonucleotides", Proc. Natl. Acad. Sci. PNAS, vol. 100, No. 8, pp. 4504-4509, 2003.

(Continued)

*Primary Examiner*—Young J Kim

(57) ABSTRACT

A method of amplifying nucleic acids and determining the amount of amplified nucleic acids uses magnetic detection. The detection can be performed during the amplification process of the nucleic acid. During the detection, the amplified nucleic acid is bound to a sensor via a biological molecule.

12 Claims, 4 Drawing Sheets

FOREIGN PATENT DOCUMENTS

| WO | WO 2005010527 A1 * | 2/2005 |
|---|---|---|
| WO | 2006054238 | 5/2006 |

OTHER PUBLICATIONS

Kohne et al: Legionella: Proceedings of the 2nd International Symposium, American Society for Microbiology, pp. 107-108, 1984.

Pierce et al: "Linear-After-The Exponential (LATE)-PCR:", PNAS, vol. 102, No. 24, pp. 8609-8614, 2005.

Hill Craig, S: "Molecular Diagnostics for Infectious Diseases", Journal of Clinical Ligand Assay, vol. 19, No. 1, pp. 43-52, 1996.

S.H. McDonough et al: "Nucleic Acid Amplification Technologies:Application to Disease Diagnosis", Biotechniques Books, pp. 113-123, 1997.

Compton, J: "Nucleic Acid Sequence-Based Ampiflication", Nature, vol. 350, pp. 91-92, 1991.

Saiki et al: "Primer-Directed Enzymatic Ampiflication of DNA", Science, vol. 239, pp. 487-491, 1988.

G. T. Walker et al: "Strand Displacement Ampiflication", Nucleic Acids Research, vol. 20, No. 7 1691-1696, (1992).

Laffler et al: "The Ligase Chair Reaction", Ann. Biol. Clinic, vol. 30, pp. 821-826, 1993.

Richard Luxton et al: "Use of External Magnetic Fields", Analytical Chemistry, vol. 76, No. 6, pp. 1715-1719, 2004.

* cited by examiner

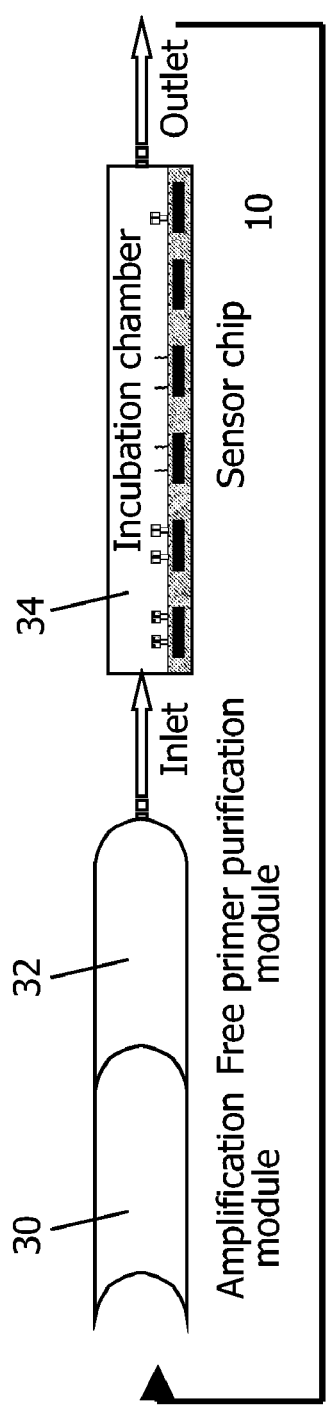
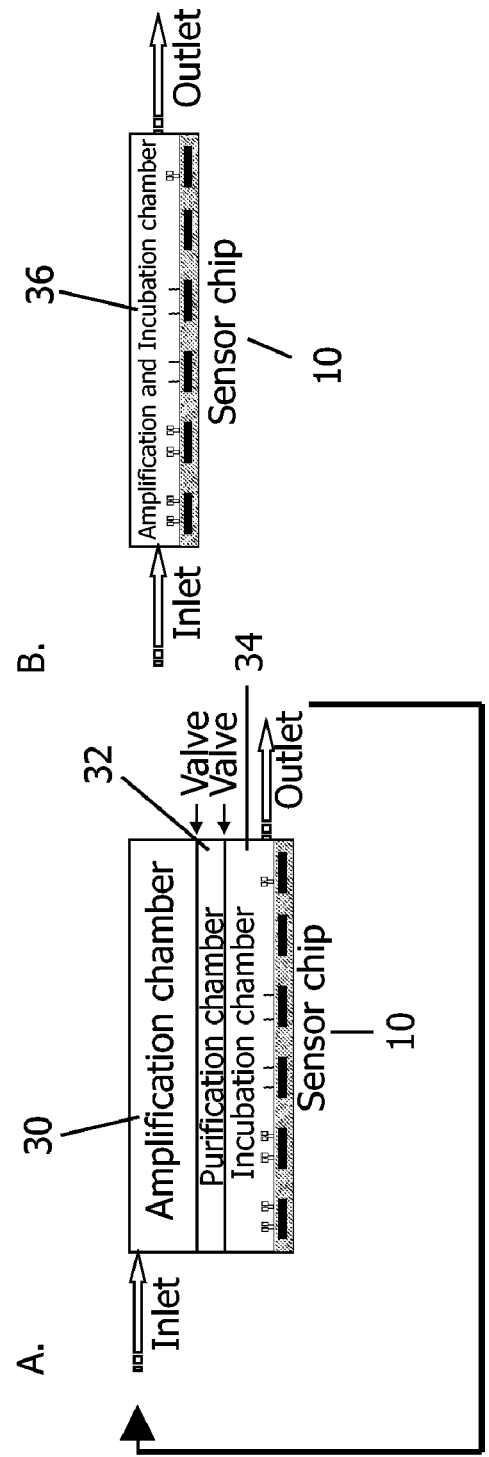
FIG.2
FIG.3

AMPLIFICATION OF NUCLEIC ACIDS WITH MAGNETIC DETECTION

The invention relates to the field of quantifying amplified nucleic acid sequences, e.g. DNA and RNA amplification, or of reagents involved in the amplification process and especially to methods and apparatus for quantifying amplified nucleic acid sequences, e.g. DNA and RNA amplification or of reagents involved in the amplification process. The invention further relates to the field of magnetic detection of biomolecules, and especially to methods and apparatus for magnetic detection of biomolecules.

Nucleic acids (RNA, DNA) can be very sensitively and specifically measured by using a biochemical amplification process. Nucleic-acid amplification and subsequent detection are complicated processes that generally require several process steps. For the detection of biological material (e.g. micro-organisms) these steps include typically (selective) enrichment, isolation/purification and identification. There are large efforts ongoing to simplify the processes and improve the analytical performance (e.g. sensitivity, specificity, speed). For example, it has been shown that it is feasible to sensitively and specifically detect the products of RNA/DNA amplification by means of ligand proteins through a combination of molecular biological techniques and immuno-detection. For signal development other assays use fluorescence, chemiluminescence or a wide variety of (immuno)sensor detectors instead of colorimetry. However, most of the assays developed are relatively complex, expensive and/or require (sophisticated) instrumentation.

A simplified extraction and amplification method combined with a lateral flow immunoassay (LFIA) detection method has been developed, which is several orders of magnitude more sensitive than gel electrophoresis and results are revealed within 5 to 15 minutes. In principle, LFIA is suited for multi-analyte detection, i.e., the screening for up to 6 specific RNA/DNA sequences in one assay device. A method based on black colloidal particles and specific ligands immobilized on nitrocellulose membranes enables the detection of 5 to 30 different parameters in a mini-array set up. The results can be digitized by flatbed scanning and image analysis.

The quantitative aspect and the dynamic range of the measurement is an important problem in biochemical amplification. This is particularly the case for exponential amplification methods such as PCR, which have a steep transition between sub-detection-level amplicon concentrations on the one hand and saturation of the biochemical amplification process on the other hand. Often the result is a yes-or-no answer rather than a precise value for the target concentration.

An improved method is Real-time PCR, wherein the concentration of amplicons is dynamically measured (e.g. with molecular beacons) during the exponential biochemical amplification process. In quantitative real-time PCR, quantitative data are derived using dedicated probe design, process control and process monitoring. The original target concentration is deduced from the time required to develop a certain signal. Disadvantages of quantitative real-time PCR are (i) the complicated assay procedure, (ii) the high cost-level per test, and (iii) the difficulty to perform assay-multiplexing.

In their most commonly used forms, the above methods (ELISA, LFIA, real-time PCR) all involve optical detection. Optical detection has several disadvantages, such as High background signals (e.g. autofluorescence from the substrate or the device material, from the sample material or from the biological materials in the test device) particularly when complex biological samples are used.

Label properties can depend on the biochemical environment (e.g. fluorescence efficiency), which complicates quantification of the measurement Error-prone interconnections between cartridge and reader.

Light scattering from the device and from the fluid sample.

Absorption of incident and emitted/reflected light depends on the optical properties of the fluid.

Sometimes expensive readout equipment is needed.

Alternative detection methods to light-based detection exist, For example magnetic sensors which detect magnetic nanoparticles are being investigated for bio-diagnostic purposes due to the following expected advantages: high analytical performance (sensitivity (biological materials have a very low magnetic background and very sensitive sensors are available)), speed (due to magnetic actuation), specificity (due to force discrimination), combined assay steps (e.g. target extraction and detection, both with magnetic particles), and easy to use (simple and reliable electrical interconnect, the sensor and reader are compact and of low cost).

Preliminary attempts have been made to combine nucleic-acid amplification with magnetic detection. WO00/61803 discloses a combination of nucleic-acid amplification followed by detection on a magnetic sensor chip. The process includes the application of stringency by magnetic forces. The solution is particularly focused on the method of Strand Displacement Amplification (SDA). EP0781346 discloses a method wherein PCR amplification is alternated with a magnetic detection method. The magnetic detection is based on the difference in migration between magnetically labeled primers and amplified DNA.

In view of the drawbacks of light-based detection there is a need for rapid, sensitive, quantitative, high dynamic range, and real-time nucleic-acid detection processes based on alternative detection methods using magnetic sensors and magnetic particles. Such methods should contain as few steps as possible, i.e. have maximum integration of biochemical processes and detection.

The invention relates to methods and tools for amplifying nucleic acids i.e. RNA or DNA and determining the amount of amplified RNA or DNA or of a reagent involved in the amplification process. In this method the step of determining the amount of the amplified nucleic acid or of a reagent involved in the amplification process is performed via magnetic detection and is performed at least one time during the amplification process of said RNA or DNA. In the method of the present invention, the step of determining the amount of the amplified RNA or DNA or of a reagent involved in the amplification process is performed via a method wherein the amplified nucleic acid or the reagent is bound to a sensor via one or more biological molecule(s).

Particular embodiments of the present invention relate to methods and tools for performing such methods as described above wherein the one or more biological molecules which is/are used to bind the amplified nucleic acid is DNA, Peptide Nucleic Acid (PNA) or RNA which specifically binds the amplified nucleic acid or amplicon. Alternatively, the biological molecule can be a protein, a vitamin, lipid or carbohydrate or can be a combination of both a nucleic acid and a protein which ensures binding of the amplicon to the sensor surface.

Particular embodiments of the present invention relate to methods and tools for performing such methods wherein the nucleic acid which is amplified by an isothermal method or by a thermocycling method.

Further particular embodiments of the present invention relate to methods and tools for performing such methods wherein the primers which are used for the amplification (amplimer) are labeled with a magnetic particle. Alternative embodiments of the invention relate to methods and tools for performing such methods wherein the amplicon is detected by way of a specific hybridization probe, which is labeled (in this embodiment the amplimers are not labeled with a magnetic particle).

The present invention further provides a kit for determining the presence of a nucleic acids, e.g. oligonucleotides or of a reagent involved in the amplification process in a sample wherein said kit comprises at least a device with a sensor surface with one or more biomolecules attached to said sensor surface, one or more oligonucleotides (DNA or RNA) whereof at least one of the oligonucleotides is coupled at least intermittently to a magnetic particle, and one or more DNA or RNA polymerase enzymes. The kit further optionally comprises an enzyme with nicking activity or can comprise an enzyme with Rnase activity (e.g.) RNAseH.

According to one embodiment of the kit of the present invention the nucleotide, e.g. oligonucleotide coupled to a magnetic particle is a primer used in the amplification thereby ensuring labeling of the amplicon during amplification.

According to another embodiment of the kit of the present invention the one nucleotide coupled to a magnetic particle is a hybridization probe which specifically hybridizes with the amplicon and by binding to the amplicon allows its detection by a magnetic sensor.

The methods and tools of the present invention allow polynucleotide determination with improved analytical performance, such as improved speed, sensitivity and specificity. The methods and tools of the present invention allow polynucleotide concentration determination with improved ease of use, such as a higher robustness, a lower error rate, simpler interconnections and lower cost.

In one aspect of the present invention and in order to measure a concentration of nucleic-acids in a sample, magnetic-particle cycling is combined with nucleic-acid amplification, taking advantage of the integration and synchronization of the magnetic cycling and the nucleic-acid amplification cycling processes (e.g. temperature cycling or reagent cycling).

The methods of the present invention may include the following steps: an optional nucleic acid extraction step, an optional magnetic pre-amplification step to determine the amount of starting nucleic acid, a nucleic acid amplification step and a detection step wherein a biomolecule (e.g. DNA or RNA) is used for binding the amplified nucleic acid, e.g. to a sensor surface or to another body.

The methods of the invention involve the detection of the amplified nucleic acids or of reagents involved in the amplification process by binding to a biomolecule which is itself bound to a sensor. The binding of the biomolecule to the sensor surface can be covalent.

According to one embodiment this process is comprises the following steps.
Amplification of nucleic acids in a bulk solution with primers covalently attached to magnetic particles and/or a sensor-chip surface.
Measurement of nanoparticles in the vicinity of a magnetic sensor (e.g. bound via a biomolecule to the sensor surface) as a function of time, and
Application of magnetic-particle cycling to allow the first bulk amplification process and the second surface detection process to take place with high efficiency,
More specifically, when using the PCR method, the method of the invention is characterized by the application of temperature cycling and magnetic force actuation to enable detection of amplification progress in near-real-time mode.

Generally, the present invention provides methods that combine amplification of nucleic acids with sensitive and real-time magnetic detection. The system is advantageous in terms of real-time detection, speed, process control, process monitoring, multiplexing, compactness, ease of use and low cost.

FIG. 2 shows an example of a magnetic sensor for detection of amplified nucleic acid sequences in a two-step configuration with modules for amplification and free primer purification followed by the magnetic sensor chip detection in accordance with embodiments of the present invention. After detection, the amplified nucleic acid is re-introduced into the amplification module.

FIG. 3 shows an example of a magnetic sensor for detection of amplified nucleic acid sequences in a real-time configuration with a single, three chamber module for amplification, purification and detection (after detection, the amplified nucleic acid re-introduced into the amplification module.) (A), or with a single, one chamber module for amplification and detection (B) in accordance with embodiments of the present invention.

Figure 4:
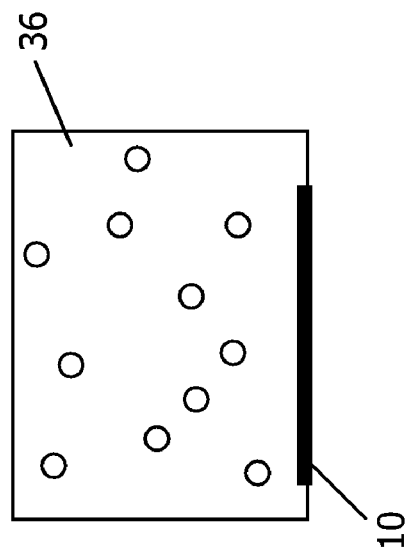

FIG. 4 shows an illustration of a device with a reaction chamber and magnetic nanoparticles (inlet and outlet are not shown) in accordance with embodiments of the present invention. The particles are actuated to go through a magnetic-particle cycling process, synchronized with the biochemical amplification process.

Figure 5:
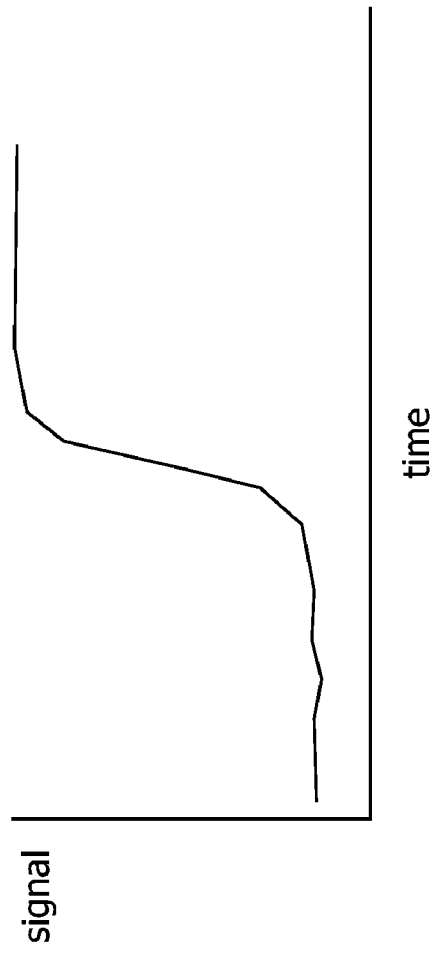

FIG. 5 shows a graph of sensor signal as a function of time.

Figure 6:
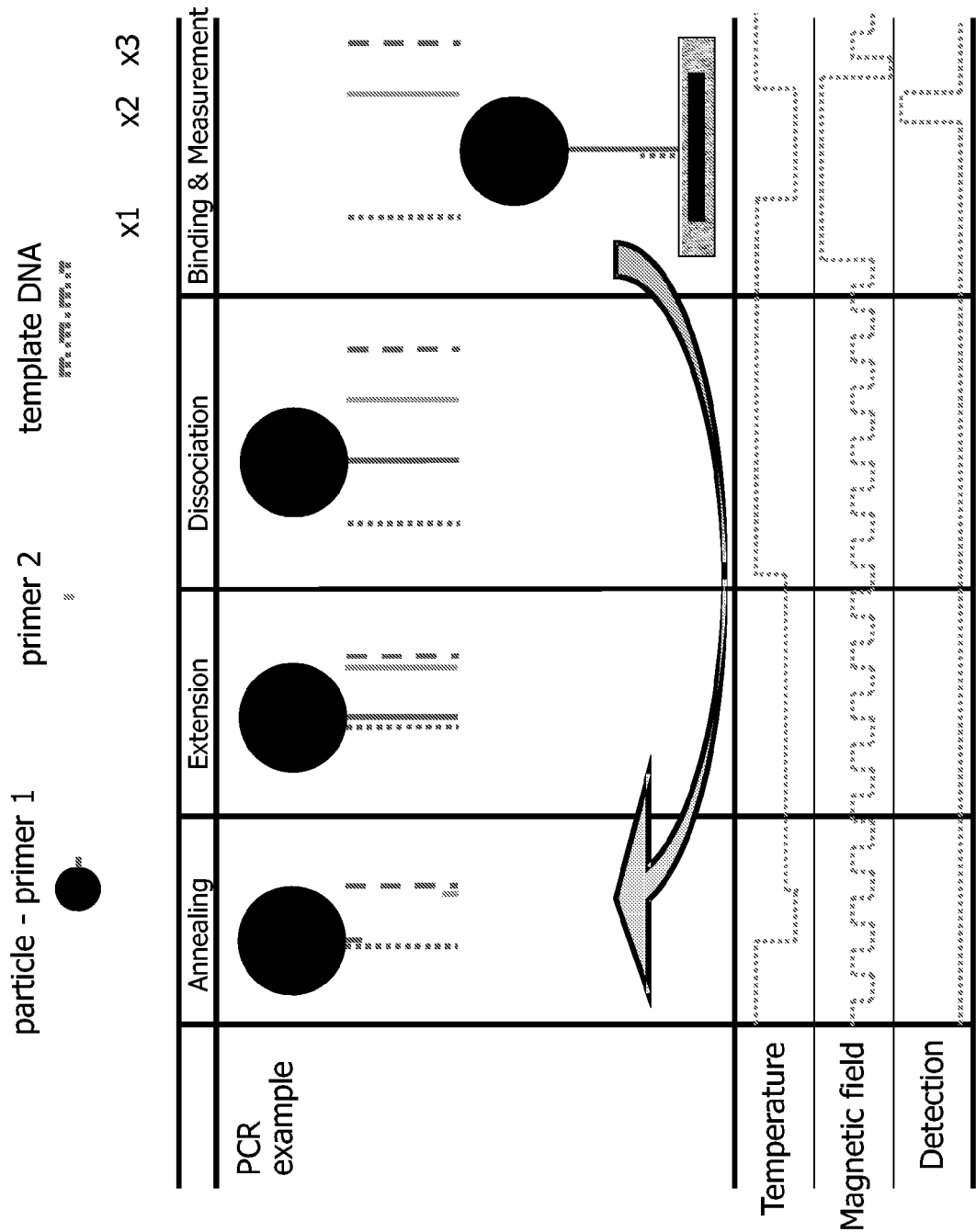

FIG. 6 shows a schematic method in accordance with an embodiment of the present invention. PCR amplification is performed in the incubation chamber above the sensor chip. Each cycle, a particular combination of temperature and magnetic field actuation is applied to measure the near-real-time status of the amplification process.

Amplimer refers to a nucleotide such as a DNA or RNA oligonucleotide used as primer for a DNA or RNA polymerase. The amplimers in a PCR reaction are generally called forward and reverse primers. A labeled amplimer refers to an amplimer which is covalently linked to a magnetic microparticle, or nanoparticle and/or a biological molecule, of which non limiting examples are biotin and fluorescein.

Amplicon refers to a nucleic acid obtained as a result of an amplification process.

Hybridization probe or hybridization primer refers to a nucleotide, such as a DNA or RNA oligonucleotide, which is used to detect amplified DNA or RNA (i.e. amplicon). In certain embodiments of the present invention a hybridization probe can be covalently linked to a magnetic microparticle or nanoparticle and/or a biological molecule.

Sensor probe or sensor primer refers to a nucleotide such as a DNA or RNA oligonucleotide, which is directly or indirectly bound to the sensor surface (i.e. the part of the device which is the proximity of a magnetic detection system) and is capable of binding the amplicon. In amplification techniques wherein the amplicon comprises RNA, an RNA sensor probe can be used to bind the amplified RNA. The binding of the sensor probe to the sensor surface can be covalent. Alternatively, the sensor probe can be linked to the sensor surface through one or more biomolecules (ligands, antibodies) covalently linked to a biological molecule.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

In one aspect the invention relates to methods wherein nucleic acid amplification is alternated with the qualitative and quantitative determination of the amplified DNA using magnetic detection and tools for performing such methods.

Methods of the present invention include the following steps:
  a nucleic acid amplification process (stepwise or continuous),
  one or more detection steps during and/or after the amplification process wherein a DNA, PNA or RNA sensor probe is used for binding the amplified nucleic acid, e.g. to a sensor surface or to another body. The binding of the sensor probe to the sensor surface can be covalent.

Optionally, the methods of the invention further comprise, prior to the amplification:
  a nucleic acid extraction step, and/or
  a magnetic pre-amplification step to determine the amount of starting nucleic acid.

According to one embodiment, the detection of the amplified nucleic acid or amplicon is ensured by incorporating the label into the amplicon. According to this embodiment the method of the invention comprises the following steps:
  amplifying nucleic acids in a bulk solution with primers attached to magnetic nanoparticles or microparticles
  contacting the amplified nucleic acid with a sensor probe attached to sensor-surface. The attachment of the primers to a sensor surface may be covalent.
  Detection or measurement of the magnetic nanoparticles or microparticles at least one time during and/or after the amplification process.

Optionally, magnetic-particle cycling is applied to allow the (first) bulk amplification process and (second) surface detection processes to take place with high efficiency.

In a specific embodiment of the invention, temperature cycling and magnetic force actuation are applied to enable detection of the amplification progress in near-real-time mode.

As indicated above, the methods of the present invention include a nucleic acid amplification step, e.g. in bulk liquid. Different amplification methods which are known in the art can be integrated in the methods of the present invention. Amplification protocols are commonly divided into target and probe types of amplification (Hill, C. S. (1996) *Journal of Clinical Ligand Assay* 19, 43-52).

'Target' amplification yields copies of the desired target sequence by synthesis from individual nucleotides using the target nucleic acid molecule as template. Examples are polymerase chain reaction (PCR), transcription mediated amplification (TMA), nucleic acid based sequence amplification (NASBA) and strand displacement amplification (SDA) (Saiki et al. (1988) *Science* 239, 487-491; Compton, J. (1991) *Nature* 350, 91-92; Walker et al. (1992) *Nucl. Acids Res.* 20, 1691-1696; McDonough et al. (1997) In: Nucleic acid amplification technologies, Eds. Lee, H., Morse, S. and Olsvik, O., Natick, Mass.: Biotechniques Books, 113-123). A variance on this method is asymmetric PCR in which only the specific DNA-strand complementary to the probe on the sensor is amplified. In this method unequal amounts of primers are added to direct the amplification to a single stranded amplification process. A variance of this method is the Linear-After-The-Exponential (LATE)-PCR (Pierce et al. (2005) PNAS, 102, 24, 8609-8614) where primer pairs are deliberately designed for use at unequal concentrations. Specific embodiments of the invention involve the amplification of a specific DNA or RNA using PCR. On the other hand 'probe types' of amplification produce modified versions of the original probes put into the reaction. An example of this approach is the ligase chain reaction (LCR) (Laffler et al. (1993) *Annales de Biologie Clinique* 50, 821-826).

In the case of PCR and LCR a thermocycler is used to denature double-stranded intermediates. Other protocols (e.g. TMA, NASBA and SDA) are isothermal and require generally only one heating device at constant temperature (e.g. waterbath or thermoblock).

Transcription methods such as TMA have several differences compared to PCR/LCR. TMA can use either RNA or single-stranded DNA directly as a target. Theoretically, these methods are faster than PCR/LCR in that they can produce a billion-fold amplification in as little as 15 minutes, while PCR/LCR can take 3-4 hours to produce a similar amount. On the other hand TMA is potentially less specific than PCR, because the process is performed at a lower temperature. Specific probes are used to compensate for this difference.

A recent technique (EXPAR) uses a combination of a heat stable nicking enzyme and a polymerase (Van Ness et al. (2003)*Proc. Natl. Acad. Sci.* 100, 4504-4509). It is an isothermal molecular chain reaction in which short oligonucleotides are generated. The method is highly sensitive and can achieve amplifications of $>10^6$-fold. The robustness, speed, and sensitivity of the exponential reaction is useful in rapidly detecting the presence of small amounts of a specific DNA sequence in a sample.

The different amplification techniques above are generally referred to as amplication processes, i.e. a process from the beginning of the amplification of a sample until the desired amount of amplicon is obtained, or until the amplimers are exhausted and/or the enzyme(s) involved in the amplification have lost their activity.

In the case of thermocycling amplification process, this process comprises as such a number of discrete amplification steps. In the case of isothermal processes, the amplification is a continuous process. By magnetic cycling with probe-labeled particles and another probe immobilized onto the sensor surface the amplified material (e.g. a single-stranded RNA oligonucleotide in the case of NASBA) can be bound to the surface to enable detection of near-real-time qualitative or quantitative data. Preferably, the probes hybridize to a sequence of the amplified material different from the amplimer sequences Alternatively, this process can be however divided into amplification steps by manipulating the temperature or by physically separating the template from the amplimers. When referring to the method of the present invention as a two-step method, a method whereby amplification (and optionally purification) and detection are performed in different units, modules or chambers of the device used. Typically, the two-step method of the invention will be performed in a device comprising an amplification module, in which amplification is performed and an incubation chamber comprising the sensor (chip) surface (FIG. 2). Optionally, the device comprises a third module wherein the free primers are purified.

According to a particular embodiment of the invention a sample is pre-treated, prior to the (first) amplification, with an RNA and/or DNA extraction step. Suitable protocols are described in reference manuals on molecular cloning (e.g. Sambrook et al. 1989). Several types of DNA or RNA extraction kits are commercially available (Pharmacia, Dynal, Waters). These extraction methods (typically making use of magnetic particles) remove disturbing compounds such as polysaccharides and polyphenols.

Also simple extraction methods can be used wherein rRNA is extracted which is present in thousands of copies in a single cell (Kohne et al. 1984) In Thornsberry et al. (Ed): *Legionella*: Proceedings of the 2nd International Symposium, Washington D.C., American Society for Microbiology, 107-108). The use of a certain pre-treatment depends on parameters such as complexity and concentration of the sample.

In a further optional step, the nucleic acid, which is initially extracted using magnetic particles, can be directly used for detection by a magnetic sensor chip, in order to determine the amount of starting material in a pre-amplification step.

The methods of the present invention further comprise a detection step using magnetic sensors. According to a specific embodiment of the method of the invention, a biomolecule is used for binding the amplified nucleic acid to a sensor surface. The detection step is performed at least once during the amplification process, and also optionally at the end of the amplification process. In continuous amplification processes the detection can be performed at certain time points during the amplification process. In stepwise amplification processes such as PCR the detection step is typically performed after the extension step. The detection step can be performed after each amplification cycle of the amplification process. In certain embodiments wherein a quantitative determination is desired, the detection step takes place in the exponential phase stage of a PCR reaction, typically between about cycle 15 to about cycle 25.

The biomolecule, used for binding the amplicon to the sensor or to a molecule allowing detection by said sensor can be a protein, a nucleic acid but also other biological compounds such as carbohydrates or vitamins (e.g. biotin).

According to a particular embodiment of the invention the amplicon is linked directly or indirectly to the sensor surface by way of a sensor probe which is an oligonucleotide specific for the amplicon. Optionally, this sensor probe is covalently linked to the sensor surface.

All types of the herein-defined probes, including the sensor probe or hybridization probe, can also be linked to other molecules such as proteins, or organic molecules, either directly to the oligonucleotide, or via attachment to a magnetic particle, which is bound to the oligonucleotide. For certain applications cleavable linkers are envisaged (e.g. chemical linkers cleavable by a reducing agent, or proteins or DNA fragments which can be enzymatically cleaved). Biological interactions which ensure binding between the biological molecules envisaged in the present invention are for example DNA/DNA binding, DNA/RNA binding, antigen-antibody binding, ligand-receptor binding, substrate-enzyme binding, inhibitor-enzyme binding, affinity binding (e.g. biotin-(strept)avidine, Zinc-His-Tag, GST-GST binding protein, etc.)

Figure 1:
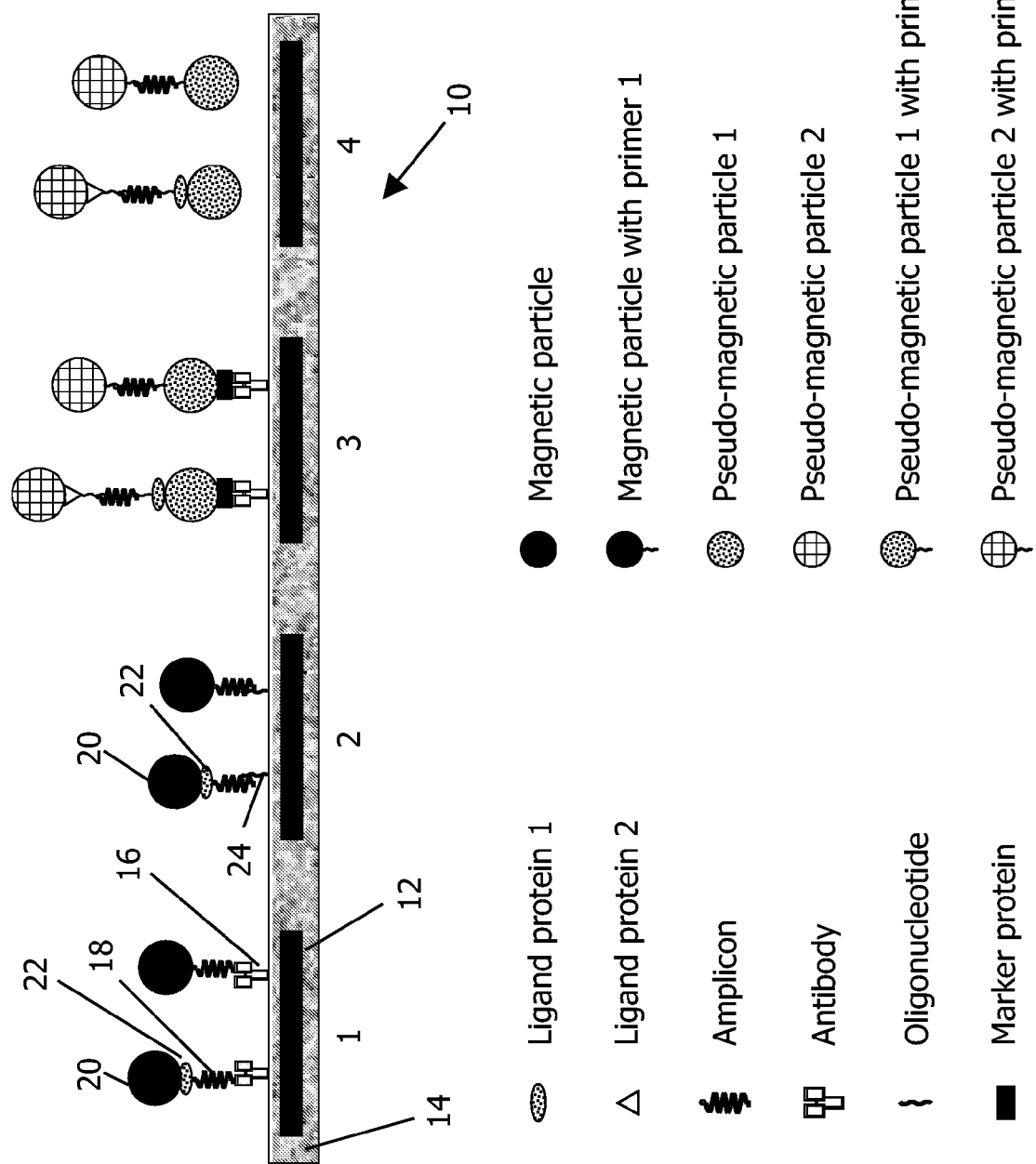
FIG. 1 shows alternative configurations of magnetic sensors for detection of amplified nucleic acid sequences for real-time detection in accordance with embodiments of the present invention.

According to one embodiment, biological molecules acting as capture molecules are immobilized on the surface of the sensor such as e.g. antibodies, a special attractive protein or polymer surface, etc. These capture molecules specifically bind the amplicons, e.g. through a tag bound to a primer (sensor probe). FIG. 1, shows in item 1 various capture schemes that can be used with the present invention. For example a capture molecule 16 such as an antibody may be bound to the surface of a sensor 10 which comprises magnetic field generators 12, e.g. magnetic bars or electromagnets embedded in a substrate 14. The capture molecule 16 may be covalently bonded to the sensor surface. The capture molecules 16 are bound to the sensor surface at least in the vicinity of the magnetic field generators 12. The substrate 14 can be a semiconductor substrate, e.g. of a "biochip". The antibody 16 binds specifically to an amplicon 18 generated by the amplification step either directly or through a tag linked to a probe specific for the amplicon. A magnetic particle 20 is bound to the amplicon 18 through a ligand protein 22 or by another means, e.g. directly (incorporation during amplification) or through a hybridization probe.

In an alternative embodiment of the present invention, the sensor-probes are linked directly to the sensor surface, this is the sensor-immobilized ligands are in fact specific oligonucleotide sequences 24 that hybridize to the end of the amplicon 18 which is not attached to the magnetic particle 20 as shown in FIG. 1, item 2. A magnetic particle 20 is bound to the amplicon 18 through a ligand protein 22 or by another means, e.g. directly (incorporation during amplification) or through a hybridization probe.

Magnetic particles 20, used in the present invention are typically in the range of 2 nm to 5 micrometer, i.e. magnetic nanoparticles or microparticles. The size of the magnetic particles 20 should not be too small, to facilitate detection and to be able to actuate the particles with applied magnetic fields. The size should also not be too large, because this can lead to non-specific binding, and sedimentation. Preferably, the particle size is in the range between 10 nm and 1 micrometer. The particles structure and shape can be any suitable one, e.g. single-magnetic-core, multi-magnetic-core, spherical, rod-shaped, etc. Magnetic particles 20 can be further coated with (bio)polymers to enhance stability and to provide functional groups for attaching a biological molecule as mentioned above.

A sensor 10 to be used in accordance with the present invention detects or measures the presence of magnetic microparticles or nanoparticles 20 in the vicinity for example within 100 µm, more preferred within 10 µm. "According to a particular embodiment, the sensor will be ten times more sensitive to nanoparticles within 1 µm of the sensor surface than to nanoparticles at a distance of 10 m from the sensor surface." The sensor 10 can be any suitable electromagnetic sensor that can detect the presence of magnetic particles, e.g. an electrode, a wire, a coil, magneto-resistive sensor, magneto-strictive sensor, Hall sensor, planar Hall sensor, SQUID, magnetic resonance sensor, etc. Preferably the sensor 10 is a magneto-resistive sensor, e.g. a giant-magneto-resistive (GMR) sensor in order to reach a high signal-to-noise ratio for magnetic fields well below 1 kA/m. The sensor can optionally be integrated in a chip.

On the sensor surface or in the proximity of the sensor surface preferably as many functions as possible are integrated, such as temperature sensing, heating, and magnetic detection. Cooling elements (e.g. Peltier element) can be integrated in the cartridge or can be part of the reader instrument. When rapid heating and cooling is desirable (e.g. PCR) the contact area of the sample liquid to the heater or cooler element is preferably as large as possible.

The strength of field and field gradient required to transfer magnetic particles through a solution depend on several parameters, e.g. the magnetic susceptibility and magnetic moment of the particles, the homogeneity and concentration of particles, the occurrence of particle-particle interactions such as clustering or chain formation, and the flow resistance in the medium. The fields can be generated by a combination of field-generating means (current wires and magnetic material) in the reader, in the cartridge, and on the chip. In our system these parameters will be selected in such a way to give repetitive transport of particles in the biological chamber during the time of the assay.

Biological bonds between a magnetic particle and another element (e.g. the sensor surface) can be probed or disrupted by generating forces or torques between the particle and the other element (see for example WO2005010527).

Magnetically labeled biomolecules are introduced (e.g. labeled primers and probes) and generated (e.g. the labeled amplicon) in the reaction mixture and are then manipulated. In particular embodiments, the magnetically labeled biomolecules are distributed and/or mixed within this mixture by applying magnetic fields. For example, magnetic-particle surface/bulk cycling in biochemical assays are used as has recently been described in an immunoassay with particle detection by a planar coil (Luxton et al. (2004) *Anal. Chem.* 76, 1715).

The present invention includes additional methods for magnetic-particle cycling on magneto-resistive sensors and methods to make the bulk as well as the surface processes more efficient, e.g. using additional agents or dedicated actuation methods as described in WO2005010527.

Biological interactions with microparticles or nanoparticles can give a strong increase of the steepness of a melting curve and enhanced specificity of detection, possibly due to co-operative effects.

Different devices are suitable for performing the methods of the present invention The device can have a flow-over or a flow-through design. A flow-through package is for example described in DE040286_EPP (filed in November 2004). Care is taken to avoid dead corners or unwanted recirculation, e.g. having smooth transitions and by avoiding flow edges with steep angles. In case a washing step is used with a washing solution, the design of the chamber preferably ensures a large refresh rate over the sensor surface, e.g. by narrowing the flow depth at the location of the sensor. The cartridge is preferably made of materials that have low non-specific binding of biomaterials, in order to avoid the loss of target material and/or reagents to the cartridge walls.

FIG. 2 illustrates one embodiment of the invention using a serial arrangement of amplification 30, purification 32 and detection 34 units. The amplification process is separated from the sensor detection step. Undesired interactions between free primers and specific ligands at the sensor surface are avoided and if necessary, free primers and other reaction contaminants remaining after the amplification process are removed in a purification module 32, consisting of, for example, silica material. According to certain embodiments the fluid in the amplification chamber is recirculated, whereby the purification module is designed to allow the amplicon to pass and maintain all other materials (e.g. the free primers) in the amplification chamber.

FIG. 3A illustrates one embodiment of the invention whereby a single device is used with three chambers 30-34, each transition separated by a controllable valve-system to allow the controlled and timely passage of the solution into the next chamber. The three chambers 30-34 and sensor chip 10 fulfill similar roles as the modules 30-34 and sensor chip 10 in the construction as depicted in FIG. 1, but here the fluids can be transferred back-and-forth between the chambers 30-34.

In a further preferred embodiment a processing and detection device is as shown in FIG. 3B, i.e., amplification and detection or measurement are performed in a single device 36, preferably in a single chamber in the vicinity of the sensor chip 10, which allows direct detection of amplicons formed. More particularly the device comprises a heat stable sensor surface, preferably with immobilized ligands linked thereto and has the ability to perform the amplification protocol at varying temperatures (e.g. PCR), or at a constant temperature (e.g. NASBA) as required by the amplification method used. Additionally, the device is adapted to allow the removal of competitive free primers if present, to avoid the occurrence of non-specific interactions such as in primer-primer complexes and to take account of the specific characteristics of magnetic particles used.

As shown schematically in FIG. 4, the present invention includes additional methods for magnetic-particle cycling on magneto-resistive sensors and methods to make the bulk as well as the surface processes more efficient, e.g. using additional agents or dedicated actuation methods as described in WO2005010527)

Modifications of the processing and detection devices are included within the scope of the present invention. In particular, other possible device geometries include the use of high-surface-area materials for the sensor surface. Further a lateral flow or flow-through architecture can be used.

The present invention is applicable in a variety of applications. A non-limiting list of applications are for example, the detection of micro-organisms (food spoilage and poisoning, and of genes encoding toxins in the agri-food-environment field; the assessment of active genes (mRNA in 'genomics' studies) in crops and fruits (quality indicators); the detection of GMO's (food safety and identification) the assessment of adulteration/fraud (determination of foreign DNA); the detection of allergenic products/contaminations; the detection of micro-organisms with environmental consequences, e.g. MRSA, *legionella, listeria*; the identification of micro-organisms in cell cultures. Applications in clinical diagnostics are for example: the detection of micro-organisms with respect to sepsis, meningitis, respiratory diseases, tuberculosis, hepatitis, AIDS, etc.; the identification of micro-organisms in cell cultures, e.g. related to the above diseases.

The invention is now illustrated with the following examples.

EXAMPLE 1

PCR Amplification Using Amplimers without Magnetic Label

After an optional nucleic acid extraction step, the amplification of nucleic acids is performed in any of the processing and detection devices mentioned above according to the PCR protocol with two specific amplimers in the solution. The amplification process results in amplicons 18 of which one of the strands hybridizes with a hybridization probe which is covalently bound to the surface of magnetic nano- or microparticles 20. Another part of this strand of the amplicon 18 hybridizes with another complementary probe, i.e. a sensor probe, attached to the sensor chip surface. The attachment may be covalent. Minimal interference is obtained when the hybridization and sensor probe hybridize with a nucleic acid sequence within the extended strand that is not complementary to the amplimers used in the amplification process. In this example, the concentration of microparticles or nanoparticles which become attached to the sensor is intermittently measured, at a particular point in a repeating sequence (cycle).

The three following steps describe a conventional PCR cycle:

Template double-strand DNA is heated to dissociate the individual strands, typically between 90 and 99° C. (denaturation).

The temperature is lowered to allow primers to anneal to the free strands, typically between 45-65 depending on the amplimer primer length and sequence (annealing).

The temperature is raised, typically to 72° C. Primers are extended along the template strands (extension).

In order to detect and measure the amplified nucleic acid, e.g. DNA, RNA the following steps are performed:

After completion of the DNA amplification, the temperature is raised to dissociate double-strand DNA.

Hybridization probes with magnetic micro- or nanoparticles are attracted from the bulk solution toward the sensor surface using a magnetic force, e.g. due to a magnetic field gradient generated by magnetic field generators 12. The DNA strand complementary to the hybridization and the detection probes, is sandwiched (via hybridization) between these probes. As a consequence the DNA strand is immobilized to the surface of the sensor and labeled with a magnetic particle.

Non-bound hybridization probes are subsequently repelled from the sensor surface by applying a magnetic force, e.g. by a magnetic field and/or magnetic field gradient with the correct slope, however the maximum force being such that it does not disrupt the DNA-DNA hybrids in the strand-hybridization probe-sensor probe complex. Typical values are in the pN range, forces in the nN range will disrupt the specific bonds (as described in WO2005010527).

The magnetic field strength of the magnetic particles attached to the hybridization probe is measured, this value being related to the amount of amplicon formed in the PCR amplification. This method allows a near-real-time PCR detection.

After the measuring step, the temperature is raised again to dissociate probe amplicon strand interactions. The nanoparticles are redistributed in the bulk solution by inverting the magnetic field whereafter they participate again in the biochemical reactions by magnetic force actuation applied. At this point the sample is denatured and ready to enter a next amplification cycle.

FIG. 5 shows a graph of sensor signal as a function of time.

For those skilled in the art it is evident that modifications of particular steps in the above process are possible. For example, the detection step is performed after each amplification step, alternatively the detection step is performed with a lower frequency or is only performed after an initial number of PCR cycles have been performed without detection step.

The above process is called 'magnetic particle and temperature cycling' as both the magnetic particles are cycled as well as the temperature. It allows micro- or nanoparticles to efficiently participate in a bulk process as well as in a surface process. In this embodiment amplicon formation and generation takes place in the bulk solution and particle detection at the sensor surface. It is a form of intermittent detection, the time between individual measurements being equal to the cycle time of the PCR procedure. By decreasing the PCR cycling time, the near-real-time situation of the amplification process becomes more accurate. Presently, state-of-the-art, miniaturized amplification requires 15 to 30 seconds per cycle.

By addition of an internal standard to the process, i.e. a known amount of a reference template and dedicated primers for comparison purposes, it is possible to make this near-real-time amplification also quantitative. Preferably, a separate spot or spots (statistically randomized) on the sensor surface is or are made specific for this internal standard. By recording the amplification efficiency (e.g. amount per time interval) a calculation of the initial amount of the unknown template DNA is possible.

In a more preferred set up the detection is performed in a regime where the amount of hybridization primers to the micro- or nanoparticles has a low amplicon coverage, i.e. on average less than one amplicon per nanoparticle. This ensures that the probability of having more than one amplicon per micro- or nanoparticle is very low and that the number of micro- or nanoparticles on the sensor can be quantitatively and accurately translated into a target concentration in the original sample.

In accordance with the present invention multiplexing may also be performed by having an array of sensors 10 with different capture molecules. In some cases the same primers can be used, in other cases different primers will be needed.

EXAMPLE 2

PCR Amplification Using Amplimers with Magnetic Label

After an optional nucleic acid extraction step, amplification of nucleic acids is performed according to the PCR protocol with amplimers of which one is coupled covalently to a magnetic particle and the other is not magnetically labeled. This example is illustrated schematically in FIG. 6. The amplification process results in one of the extended strands being labeled to magnetic micro- or nanoparticles via the attached primer.

In this example, the concentration of micro- or nanoparticles attached to the sensor 10 is intermittently measured, at a particular point in a repeating sequence (cycle).

The steps describing a preferred design and procedure and the additional options indicated according to this embodiment are essentially the same as described for the procedure in Example 1, although apart from the amplimers only one additional probe (sensor probe) is necessary, attached covalently to the sensor chip surface. This sensor probe can comprise the same sequence as an amplimer oligonucleotide or can overlap with the sequence of an amplimer oligonucleotide, as depicted in FIG. 6. Alternatively, the sensor probe hybridizes to a sequence of the amplified DNA different from the sequence to which an amplimer binds.

As an alternative of the above: the concentration of magnetic particles bound to the sensor during a detection step, has a relationship with the original target concentration. In other words, for a given assay time and time of the detection process, the concentration of particles on the sensor by binding to a formed amplicon strand indicates the original target concentration. Another way of measuring the amount of amplicon formed is the detection of the amount of amplimers remaining at a particular assay time. If the particle-bound amplimer is targeted for this approach, the concentration of bound particles would decrease upon increasing concentration of amplicons formed during the amplification process. Here an example of such an assay is given:

One type of amplimer is coupled covalently to a magnetic particle. On the sensor, probes are immobilized which have been selected to bind to this amplimer. So initially the particles with this covalently-coupled amplimer can bind to the sensor with a high binding rate. As the amplification process proceeds, more particle bound amplimers will be extended to full amplicons. As a consequence, the probability that a particle binds to the sensor decreases, driven by the lower number of accessible amplimers on the particle and/or due to steric hindrance by the amplicons bound to the particle.

EXAMPLE 3

Microarray Applications of the Invention

The procedures described in the previous examples enable the detection of amplified genetic material by magnetic field cycling and in some cases temperature cycling. Any of these methods is excellently suited to be applied in micro-array applications. The strength of interaction between probes immobilized at the sensor surface of the array and amplicons from the sample solution (in this case attached to magnetic nanoparticles) is more or less proportional to the extent of complementarity between probe and amplicon. By applying different forces across the array (e.g. different magnetic forces that depend on the array position) or by varying the forces as a function of time, various types of array sub-spots are identified, e.g. from spots loosing the attached amplicons and magnetic nanoparticles at low forces (e.g. nonspecific or highly-degenerative hybridization) up to spots with a very powerful binding between probe and amplicon (e.g. high complementarity). In this last case the magnetic signal is still recordable as a consequence of the magnetic particles immobilized at these particular spots.

In a micro-array set up, in which specific probes are immobilized onto very small and discrete parts of the sensor surface, the chance of collisions between a particular probe and a labeled magnetic particle having the specific complementary amplicon/ligand attached or bound, is very small. Magnetic force cycling with velocity components perpendicular to the sensor surface will increase the concentration of specific binding pairs (i.e., surface probe and amplicon/ligand labeled magnetic particle) in a small volume above the sensor surface. However, movement of particles parallel to the sensor surface is restricted (also as a result of the magnetic field). Consequently, the interaction of specific binding pairs in relation to the amplification process necessary to give measurable results is an inefficient process in the micro-array set up.

To overcome this drawback another embodiment of the micro-array format is presented in which magnetic forces and velocities are applied with components parallel to the sensor surface, intermittently or in a co-ordinated way with the perpendicular components, to move the particles horizontally and in close proximity over the sensor surface to further increase collisional contacts.

In addition to adjusting the temperature to influence the binding efficiency magnetic field actuation can be used to give added value to sub-divide interactions at a particular temperature. This may enable the detection of SNPs or other changes of nucleic-acid sequence, so that gene-differences can be detected without sequence analysis (note that a sequence analysis may be used as a confirmation test). This may also enable a more sensitive and more accurate description of up- and down-regulated genes, i.e., a lower number of key-genes with respect to the particular physiological parameter studied in the micro-array experiment. This may also enable a more precise identification of micro-organisms, pathogens, or other biological material.

The invention claimed is:

1. A method comprising the act of:
    amplifying a nucleic acid using one or more amplimers to form amplicons;
    labeling said amplicons with magnetic particles;
    binding the amplicons to a sensor surface via a biological molecule, wherein during the binding act, increasing collisions between the amplicons labeled with the magnetic particles and the biological molecule bound to the sensor surface by magnetic force cycling; and
    determining an amount of the amplicons bound to the sensor surface via magnetic detection;
    wherein the magnetic detection is performed to detect the amplicons with the magnetic particles at least one time during the amplifying act;
    wherein the magnetic force cycling includes cycling with velocity components perpendicular to the sensor surface to increase concentration near the sensor surface of the amplicons labeled with the magnetic particles and bound to the sensor surface and restrict movement of particles parallel to the sensor surface, while intermittently cycling with velocity components parallel to the sensor surface in a coordinated way with the cycling of the perpendicular components to move the concentrated amplicons labeled with the magnetic particles horizontally and in close proximity over the sensor surface to further increase the collisions.

2. The method according to claim 1 wherein said biological molecule is DNA.

3. The method according to claim 1, wherein the nucleic acid is amplified by an isothermal method.

4. The method according to claim 1, wherein the nucleic acid is amplified via a thermocycling method.

5. The method according to claim 1, wherein one amplimer is labeled with a magnetic particle.

6. The method according to claim 1, wherein the amplicons are detected using a magnetically labeled hybridization probe.

7. A kit of parts for determining an amount of a nucleic acid in a sample or of a reagent involved in an amplification process to form amplicons, said kit comprising at least:
    a device with a sensor surface with one or more biomolecules attached to said sensor surface,
    oligonucleotides of which at least one is coupled to a magnetic particle, and
    one or more DNA or RNA polymerase enzymes,
    wherein the device includes a magnetic force generator configured to increase collisions between the amplicons labeled with magnetic particles and the biomolecules attached to the sensor surface by magnetic force cycling, wherein the magnetic force cycling includes cycling with velocity components perpendicular to the sensor surface to increase concentration near the sensor surface of the amplicons labeled with the magnetic particles and bound to the sensor surface, while intermittently cycling with velocity components parallel to the sensor surface in a coordinated way with the cycling of the perpendicular components to move the concentrated amplicons labeled with the magnetic particles horizontally and in close proximity over the sensor surface to further increase the collisions.

8. The kit according to claim 7, further comprising an enzyme with nicking activity.

9. The kit according to claim 7, further comprising an enzyme with RNAse activity.

10. The kit according to claim 7, wherein said at least one oligonucleotide is an amplimer.

11. The kit according to claim 7, wherein said at least one oligonucleotide is a hybridization probe.

12. The kit according to claim 7, wherein the sensor surface is part of a microarray.

* * * * *